(12) United States Patent
Hettiarachchy et al.

(10) Patent No.: US 7,160,580 B2
(45) Date of Patent: Jan. 9, 2007

(54) ORGANIC ACIDS INCORPORATED EDIBLE ANTIMICROBIAL FILMS

(75) Inventors: Navam S. Hettiarachchy, Fayetteville, AR (US); Eswaranandam Satchithanandam, Fayetteville, AR (US)

(73) Assignee: The Board of Trustees for the University of Arkansas, Little Rock, AR (US)

( * ) Notice: Subject to any disclaimer, the term of this patent is extended or adjusted under 35 U.S.C. 154(b) by 396 days.

(21) Appl. No.: 10/657,692

(22) Filed: Sep. 8, 2003

(65) Prior Publication Data

US 2005/0053640 A1    Mar. 10, 2005

Related U.S. Application Data

(60) Provisional application No. 60/409,182, filed on Sep. 8, 2002.

(51) Int. Cl.
*B05D 1/18* (2006.01)
*A23B 7/16* (2006.01)

(52) U.S. Cl. .................................. 427/430.1; 426/307
(58) Field of Classification Search .................... None
See application file for complete search history.

(56) References Cited

U.S. PATENT DOCUMENTS 5,433,960 A * 7/1995 Meyers ........................... 426/5
6,656,493 B1 * 12/2003 Dzija et al. .................. 424/439
6,740,332 B1 * 5/2004 Zyck et al. .................. 424/435

FOREIGN PATENT DOCUMENTS

WO    WO 03/043659 A1 * 5/2003

OTHER PUBLICATIONS

Altekhruse, S.F. et al., 1994 Food-borne infections in individuals with human immunodeficiency virus. South Med. J. 87:169-173.
Misubu, B., et al., 1993 Serological evidence of previous *Campytobacter jejuni* infection in patients wiht the Guillain-Barre syndrome. Ann. Intern. Med. 118:947-953.
Torres, J.A. 1994 Edible films and coating from proteins. In Hettiararchchy N.S., Ziegler, G.R., Eds. Protein functionalilty in food systems. pp. 467-507.
Ariyapitipuri et al. 1999 Micribial shelf life determinatin of vacuum-packaged fresh beef treated with polylactic acid, lactic acid, and nisin solutions. J. Food Prot. 62(8).
Ayres et al., 1999 Effect of permeabilizers on antibiotic sensitivity of *Pseudomonas aerunosa*. Letters in Applied Microb. 28:13-16.
Boussouel et al. 1999 Response Surface Methodology, an approach to predict the effects of a lactoperoxidase system, Nisin . . . J. Appl. Microbiol. 86:642-652.
Brackett, R.E. 1999 incidence, contributing factors, an control of bacterial pathogens in produce. Post Harvest Biol. Tech. 15:305-3111.

Brody, A.L. 2002 IFT Annual Meeting & IFT Food Expo Preview, Packaging, Food Tech. 56(5):112-115.
Brody, a.L. 2001 Produce and Technology, Packaging. Food Tech. 55:104-105.
Cagri et al. 2001 Antimicrobial, mechanical and moisture barrier properties of low pH whey based edible films containing p-Aminobenzoic or sorbic acids, J. Food Sci. 66(6):865.
Cherrington et al. 1991 Short-chain organic acids at pH 5.0 kill *E. coli* and *Salmonella spp*. without causing membrane perturbation. J. Appl. Bacteriol. 70:161-165.
Cherry, J.P. 1999 Improving the safety of fresh produce with antimicrobials. Food Tech. 53(11):54-58.
Cutter et al. 1995a Treatments with nisin and chelators to reduce *Salmonella* and *E. coli* on beef. J. Food Protection 57(9):1028-1030.
Cutter et al. 1995b Population reduction of gram-negative pathogens following treatments with nisin and chelators under various conditions. J. Food Protection 58:977-983.
Fanbg et al. 2000 Effects of chelators, organic acid and storage temperature on growth of *E. coli* 0157:H7 in ground beef . . . J. Food and Drug Analysis 8(3):187-194.
Farid et al. 1998 Organic acid dipping of catfish fillets: Effects of color, microbial load and Listeria monocytogens. J. Food Prot. 61(11)1470-1474.
Farber et al. 1991 Listeria monocytogens, a food-borne pathogen. Microbial Reviews 55:476-511.
Good, H. 2002 Solving color measurements challenges of the food inductry. Junterlab http://www.hunterlab.comWhatsNew/Food%20Industry.pdf accessed Jun. 28, 2003.
Han, J.H. 2000 Antimicrobial food packaging. J. Food Tech. 54(23):56-65.
Ingram et al 1995 The preservation action of acid substances. Food Chem. Ind. 42:1154-1160.
Lerthangkul et al 1996 Edible coating effects on post harvest quality of green bell peppers. J. Food Sci. 61(1):176-179.
Miller etal 1996 Sporostatic, sporocidal and heat sensitizing action of malic acid against spores of proteolytic *Clostridium botulinum*. J. Food Prot. 59(2):115-120.
Padgett et al. 1998 Incorporation of food-antimicrobial compounds into biodegradable packaging films. J. Food Prot. 61(10)1330-1335.
Phillips, C.A. 1999 The effect of citric acid, lactic acid, sodium, citrate and sodium lactate, alone and in combination with nisin . . . Letter in Appl. Microb. 29:242-428.

(Continued)

*Primary Examiner*—Robert A. Wax
(74) *Attorney, Agent, or Firm*—Angela Foster, Esq.

(57) ABSTRACT

The present invention provides an edible film and film solution comprising incorporated organic acids; protein and glycerol useful for coating raw whole fruit, fresh cut fruit, vegetables, meat, poultry, seafood, cereals, nuts, etc. Moreover, the edible films of the present invention can inhibit pathogen growth including *Listeria monocytogens, Salmonella gaminara* and *E. coli* 0157:H7. In a preferred embodiment, the edible film comprises 0.9% glycerol; 10% soy protein; and 2.6% malic acid. The present invention also provides a method for coating comestible products with edible films without masking the color but increasing the shelf-life.

59 Claims, 7 Drawing Sheets
(4 of 7 Drawing Sheet(s) Filed in Color)

OTHER PUBLICATIONS

Rhim et al. 2000 Solubility, tensile and color properties of modified soy protein films. J. Agric Food Chem. 48:4937-4941.

Richards et al. 1995 Activity of p-aminobenzoic acid compared with other organic acids against selected bacteria. J. Appl. Bact. 78(3):209-215.

Roe et al. 1998 Pertubation of anion balance during inhibition of growth of *E. coli* by weak acids. J. Bact. 180:767-772.

Sirugusa et al. 1993 Inhibition of Listeria monocytogensm *Salmonella typhimurium* and *E. coli* 0157:H7 on beef . . . J. Food Safety 13(2):147-158.

Zhuang et al. 1996 Inactivation of *Salmonella montevideo* on tomatoes by applying cellulose-based edible films. J. Food Prot. 59(8):808-812.

* cited by examiner

Optimization of Soy Protein and Glycerol Concentration for Film

Preparation of Soy Protein Film with Organic Acid Incorporation

Preparation of Soy Protein Coating Solutions

ORGANIC ACIDS INCORPORATED EDIBLE ANTIMICROBIAL FILMS

1. GOVERNMENTAL INTEREST

This invention was funded in part by grants from the Cooperative State Research, Education and Extension Service, United States Department of Agriculture (00-51110-9748). The United States government may have certain rights in this invention.

2. FIELD OF INVENTION

The present invention relates to an edible film that replaces glycerol with organic acids naturally present in fruits. More specifically, the present invention provides organic acid incorporated edible films that are effective against a wide spectrum of pathogens and can be used to coat raw whole or fresh cut fruits and vegetables, meat, poultry, seafood, cereals, nuts, etc.

3. BACKGROUND OF THE INVENTION

In the United States, each year food-borne illness affects about 6 to 80 million people, causing 9,000 deaths and an estimated cost of 5 billion dollars. Outbreaks of food-borne pathogens including *Listeria monocytogens, Salmonella gaminara* and *E. coli* 0157:H7 are of great concern to the food industry and the general public because they are reported present in poultry, meat and fresh fruits and vegetable products (Altekruse et al., 1994; Mishu et al., 1993). In particular, Listeriosis causes miscarriages and result in meningitis in patients with chronic underlying disease (Mishu et al., 1993); *Salmonella* can cause septicemia and produce typhoid or typhoid like fever in humans and *E. coli* 0157:H7 produces potent toxins causing damage to the lining of the intestine leading to acute hemorrhagic colitis, hemolytic uremia syndrome, and thrombotic thrombocytopenic purpura.

During 2001, a total of 13,705 laboratory-diagnosed cases of 10 food-borne diseases under surveillance were identified including 5,198 of *Salmonella*, 565 of *E. coli* 0157:H7 and 94 of *Listeria* (Center of Disease Control, 2002). Post-processing contamination of microorganism on the surface of food products led to recalls and consequent economic losses for the food industry. During January 1999 to October 2000, 63 of 97 Class I recalls of cooked/ready-to-eat meats were due to *Listeria* contamination. *E. coli* 0157:H7 was responsible for outbreaks involving fermented meat products (Tilden et al., 1996) and fresh products (Besser et al., 1993). While 32,021 *Salmonella* isolates were reported to the Public Health Laboratory Information System during 2000. Therefore, simple economical and effective means of inhibiting the growth of food-borne pathogens in food products is a longfelt need.

Edible films can increase the shelf-life of foods by providing barring properties against migration of moisture, gases, and vapor, functioning as a carrier of food ingredients additives and antimicrobial agents and offering mechanical protection to foods. However, there is limited knowledge about the utilization of edible films as carriers for the release of antimicrobials at varying rates to enhance pathogens inhibition and extend product shelf-life.

Components of edible films and coating are divided into three categories, including hydrocolloids, lipids and composites. Suitable hydrocolloids include proteins and carbohydrates. Proteins, lipid, polysaccharide and composite are based on the nature of the material used for film production. Each film or coating type provides its own unique functional characteristics and is best suited to a specific food application.

Plasticizers are necessary to produce protein or polysaccharide-based films that possess a desirable mechanical strength and flexibility for handling (Torres, 1994). Glycerol is one of the most commonly used plasticizer for producing films. In order to produce an easily handled film, usually, 25–50% glycerol is required. However, edible films comprising this concentration of glycerol can impart a faint sweet flavor. Yet, films with bland taste are desirable for multipurpose applications. Therefore, an edible film with limited glycerol content that inhibits a wide spectrum of pathogens and increases shelf-life is desirable.

Edible film coating can protect fresh produce from microbial spoilage delay ripening and extend shelf-life (Brody 2002). Color is a primary actor affecting consumer selection of fresh produce (Good 2002). Therefore, coating with edible films to prevent survival of pathogen on the surface of fresh produce should not have any adverse effect in masking the color.

Discussion or citation of a reference herein shall not be construed as an admission that such reference is prior art to the present invention.

4. SUMMARY OF THE INVENTION

Accordingly, this invention relates to the present inventors' surprising ability to reduce the concentration of glycerol in edible films by 75% and produce films that demonstrate effective inhibition of a wide spectrum of pathogens including *Listeria monocytogens, Salmonella gaminara* and *E. coli* 0157:H7 by replacing glycerol with organic acids naturally present in fruits. More specifically, the present invention provides an edible film comprising only 0.9% glycerol; proteins or hydrocolloids; and incorporated organic acid. In particular, the proteins of the edible film of this invention are selected from a group consisting of soy, whey, rice bran extract, egg albumen and wheat protein and the hydrocolloids are selected from a group consisting of carboxymethyl cellulose, alginate, caragenan and pectin. Further, the organic acid of the present invention is selected from a group consisting of malic, lactic, citric and tartaric acids. In one embodiment, the present provides an edible film comprising 7.0 to 16.5 gram weight of protein; 0.63 to 1.5 grams weight of glycerol; and 1.82 to 4.3 grams weight organic acid. In another embodiment, the present edible film comprises 1.5 to 7.5 ) grams weight of hydrocolloid; 0.14 to 0.68 grams weight of glycerol; and 0.40 to 1.95 grams weight organic acid.

Still further, the present invention provides methods for making an organic acid incorporated edible antimicrobial film solution comprising mixing protein or hydrocolloid in water; adding glycerol; heating the mixture to a desirable temperature to create a film solution; and adding an organic acid. In a preferred embodiment, the method of the present invention comprises mixing soy protein of the concentration of 2.6% in water; adding glycerol of a concentration of 0.9%; heating the soy protein and glycerol mixture to 85° C. thereby creating a film solution; and adding malic acid to a final concentration of 2.6% of the total weight.

This invention also relates to these inventors' ability to determine the maximum thickness of an edible film coating that can be applied on comestible products such as but not limited to produce, vegetables, meats and processed foods without masking its color and extend the shelf-life.

5. DESCRIPTION OF THE DRAWINGS

The patent or application file contains at least one drawing executed in color. Copies of this patent or patent application publication with color drawing(s) will be provided by the Office upon request and payment of the necessary fee.

6. DETAILED DESCRIPTION OF THE INVENTION

Figure 1:
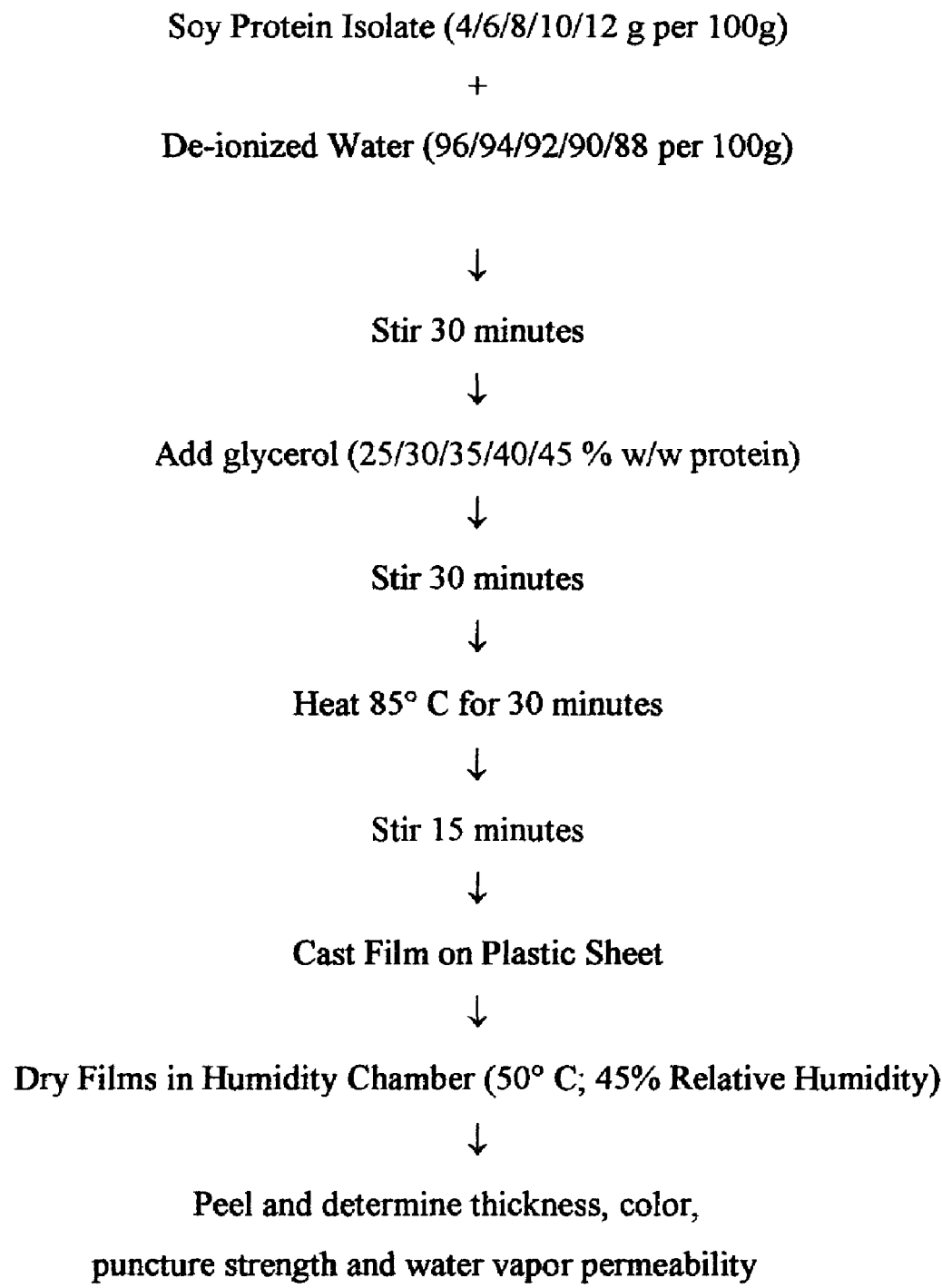
FIG. 1 is a schematic representation showing the steps for optimizing soy protein and glycerol concentrations for preparing films.

This section presents a detailed description of the invention and its applications. This description is by way of several exemplary illustrations, in increasing detail and specificity, of the general methods of this invention. These examples are non-limiting, and related variants will be apparent to one of skill in the art.

It should be understood that various changes and modifications to the presently preferred embodiments described herein will be apparent to those skilled in the art. Such changes and modifications can be made without departing from the spirit and scope of the present invention and without diminishing its attendant advantages.

Accordingly, the present invention provides an edible film comprising incorporated organic acids; protein and glycerol wherein the organic acids are capable of inhibiting pathogens.

The film of the present invention includes soy protein, rice bran extract, wheat gluten protein, egg albumen, whey, carboxymethyl cellulose, algimate, carageenan and pectin. These films can serve as vehicles to carry: (a) antimicrobials; (b) antioxidants; (c) flavor; (d) color; (e) nutraceuticals and functional ingredients; (f) drugs; (g) nutrients; and (h) packaging in wide range of products.

The film solution can be used as coatings in meat, poultry, seafood, minimally processed fruits and vegetable products to minimize or prevent the growth of pathogens including *Listeria monocytogens, Salmonella*, and *E. coli* 0157:H7. Coatings can be invisible or visible depending on the thickness of the edible film. In particular, malic acid incorporated soy protein caused 2.48, 7.52 and 2.28 log reductions of *Listeria monocytogens, Salmonella* and *E. coli* 0157:H7, respectively. Malic acid can be incorporated into a film to partially replace glycerol, reduce pH of the film and to improve antimicrobial activity against *Listeria monocytogens, Salmonella* and *E. coli* 0157:H7.

Antimicrobial studies of the present film revealed increased inhibition of *L. monocytogens* in the presence of 0.9; 1.8 and 2.6% of citric, malic and tartaric acids compared to control (without organic acid) at pH 4.55, 3.85 and 3.35. Moreover, films with 2.6% organic acids without nisin also demonstrated the same level of inhibition as with nisin. Films with 2.6% organic acids without nisin revealed higher levels of anti-*salmonella* activity. *E. coli* 0157:H7 was also inhibited by incorporation of lactic acid at 1.8 and 2.6% and malic acid at 2.6%.

Therefore, one embodiment of the present invention provides an organic acid incorporated edible antimicrobial film wherein the organic acid is selected from a group consisting of malic, lactic, citric and tartaric acids.

In another embodiment of the present invention, the concentration of organic acid is 0.40 to 4.3 g weight.

Incorporation of nisin (6400 IU/g protein) did not influence the susceptibility of *Salmonella gaminara* to lactic acid but decreased susceptibility to malic and tartaric acids. *Listeria monocytogens* and *E. coli* 0157:H7 were more susceptible to malic acid (2.6%) without nisin. However, incorporation of nisin decreased the susceptibility of *Listeria monocytogens* and *E. coli* 0157:H7 to malic acid. Therefore, in a preferred embodiment of the present invention, the edible film comprises malic acid wherein the concentration of malic acid is between 0.40 to 4.3 grams.

Studies of the present invention revealed that increasing amounts from 0.9 to 2.6% citric, lactic and malic acids had no effect on the mechanical strength of the edible film. Therefore, in yet in another embodiment, the edible film of the present invention comprises 2.6% glycerol and 2.6% inorganic acids wherein the organic acids are selected from a group consisting of citric, lactic and malic acids. In a preferred embodiment, the film has tensile strength of 3 to 30 MPa. Further, the thickness of the edible film ranges from 13–160 micrometers. Accordingly, conditions can be optimized to produce thicker films with a variety of flavors for fruit-roll-ups and other products in which nutraceuticals can be impregnated. In another preferred embodiment, the concentration of malic acid is 2.6% w/w.

Soy protein was selected because of its suitability to produce films at a wide range of pH and additives without any adverse effect on solubility. Therefore, in one embodiment, the edible film comprises protein wherein the protein is soy protein.

Studies of the present invention revealed that optimum concentrations of soy, whey, wheat proteins and carboxymethyl cellulose to produce homogenous films were 10 g; 7 g; 16.5 g; 1.5 g per 10 g, respectively. In a preferred embodiment, the concentration of soy protein is 1.5 to 16.5 grams per 100 grams. Therefore, in yet another embodiment of the present invention, the concentration of soy protein is 10% weight. Still further, another embodiment of the present invention provides an edible film comprising hydrocolloid wherein the hydrocolloid is carboxymethyl cellulose. In a preferred embodiment of the present invention, the concentration of carboxymethyl cellulose is 1.5%.

The present invention demonstrates that plasticizer glycerol (2.6% of 3.5% w/w) can be partially replaced with organic acid (2.6% w/w). Moreover, optimum concentrations of glycerol to produce films with elasticity and mechanical strength were 30%; 35%; 15%; 15% w/w of soy, whey protein, wheat gluten and carboxymethyl cellulose, respectively. Therefore, in a preferred embodiment, the present edible film comprises glycerol wherein the glycerol is a concentration between 0.14 to 1.5 grams per 100 grams. Glycerol concentrations below 15% produced brittle wheat gluten and cellulose films. Yet, glycerol concentrations below 35% and 30% produced brittle whey protein and soy protein films, respectively. In another embodiment, glycerol is present in a concentration of 0.9% weight.

The present invention further provides a method for making an organic acid incorporated edible antimicrobial film solutions comprising mixing protein or hydrocolloid in water; adding glycerol; heating said mixture to 60° to 85° C. thereby creating a solution; and adding organic acid.

In a preferred embodiment, the present invention provides a method for making an organic acid incorporated edible antimicrobial film solutions comprising mixing protein in a range of 7.0 to 16.5 weight in water; adding glycerol of range of 0.63 to 1.5 weight; heating the mixture to a temperature between 60° to 85° C. thereby creating a solution; and adding organic acid of a concentration of 1.82 to 4.3 weight. In another embodiment of the present method, the mixture is heated to 85° C. for 30 minutes.

In one embodiment of this method, the pH of the solution is lowered to a pH of about 3.3 using malic acid.

In another embodiment, the organic acid of the present invention is selected from a group consisting of citric acid, lactic acid, malic acid and tartaric acid. In a preferred embodiment, the organic acid is malic acid. In yet another embodiment, the concentration of malic acid is 2.6% weight.

In still another embodiment of the present invention, the protein of the present edible film is selected from a group consisting of soy, whey, rice bran extract, egg albumen and wheat protein. In a preferred embodiment, the protein is soy protein. In another embodiment, soy protein is present in the concentration of 10% weight.

The present invention also provides a method for making an organic acid incorporated edible antimicrobial film solutions comprising mixing hydrocolloid in a range of 1.5 to 7.5 weight in water; adding glycerol of range of 0.14 to 0.68 weight; heating the mixture to a temperature between 60° to 85° C. thereby creating a solution; and adding organic acid of a concentration of 0.40 to 1.95 weight. In another embodiment of the present method, the mixture is heated to 85° C. for 30 minutes.

In one embodiment of this method, the pH of the solution is lowered to a pH of about 3.3 using malic acid.

In another embodiment, the organic acid of the present invention is selected from a group consisting of citric acid, lactic acid, malic acid and tartaric acid. In a preferred embodiment, the organic acid is malic acid. In yet another embodiment, the concentration of malic acid is 2.6% weight.

In still another embodiment of the present method, the hydrocolloid of the present edible film is selected from a group consisting of carboxymethyl cellulose, alginate, caragenan and pectin. In a preferred embodiment, the protein is carboxymethyl cellulose. In another embodiment, carboxymethyl cellulose is present in the concentration of 1.5% weight.

The quality of fresh food is usually judged by its appearance such as the color of produce and meats. However, the thickness of edible films will affect the color and internal gas composition of fresh produce. Therefore, the present invention also provides a method for coating comestible products with an organic acid incorporated edible antimicrobial film solution without masking the color comprising mixing protein or hydrocolloid in water; adding glycerol; heating said mixture to 60° to 85° C. thereby creating a solution; adding organic acid; and applying the solution to comestible product.

On skilled in the art could apply the solution in many manners including but not limited to dipping; spraying; layering; dripping; blowing; etc.

In a preferred embodiment, the present invention provides a method for coating comestible products with an organic acid incorporated edible antimicrobial film solution without masking the color comprising mixing hydrocolloid in a range of 1.5 to 7.5 weight in water; adding glycerol of range of 0.14 to 0.68 weight; heating the mixture to a temperature between 60° to 85° C. thereby creating a solution; adding organic acid of a concentration of 0.40 to 1.95 weight; and applying the solution to comestible product. In one embodiment, the solution is applied in the range of 8–40 μm. In another embodiment of the present method, the mixture is heated to 85° C. for 30 minutes.

In one embodiment of this method, the pH of the solution is lowered to a pH of about 3.3 using malic acid.

In another embodiment, the organic acid of the present invention is selected from a group consisting of citric acid, lactic acid, malic acid and tartaric acid. In a preferred embodiment, the organic acid is malic acid. In yet another embodiment, the concentration of malic acid is 2.6% weight.

In still another embodiment of the present invention, the protein of the present edible film is selected from a group consisting of carboxymethyl cellulose, alginate, caragenan and pectin. In a preferred embodiment, the protein is carboxymethyl cellulose. In another embodiment, carboxymethyl cellulose is present in the concentration of 1.5% weight.

The present invention provides a method for coating comestible product with an organic acid incorporated edible antimicrobial film solutions comprising mixing protein in a range of 7.0 to 16.5 weight in water, adding glycerol of range of 0.63 to 1.5 weight, heating the mixture to a temperature between 60° to 85° C. thereby creating a solution; adding organic acid of a concentration of 1.82 to 4.3 weight; and applying the solution to comestible product. In another embodiment of the present method, the mixture is heated to 85° C. for 30 minutes.

In one embodiment of this method, the pH of the solution is lowered to a pH of about 3.3 using malic acid.

In another embodiment, the organic acid of the present invention is selected from a group consisting of citric acid, lactic acid, malic acid and tartaric acid. In a preferred embodiment, the organic acid is malic acid. In yet another embodiment, the concentration of malic acid is 2.6% weight.

In still another embodiment of the present invention, the protein of the present edible film is selected from a group consisting of soy, whey, rice bran extract, egg albumen and wheat protein. In a preferred embodiment, the protein is soy protein. In another embodiment, soy protein is present in the concentration of 10% weight.

The present invention also provides a method for coating comestible product with an edible antimicrobial film solutions comprising mixing protein in a range of 7.0 to 16.5 weight in water; adding glycerol of range of 0.63 to 1.5 weight; heating the mixture to a temperature between 60° to 85° C. thereby creating a solution; and applying the solution to comestible products. In another embodiment of the present method, the mixture is heated to 85° C. for 30 minutes.

In still another embodiment of the present invention, the protein of the present edible film is selected from a group consisting of soy, whey, rice bran extract, egg albumen and wheat protein. In a preferred embodiment, the protein is soy protein. In another embodiment, soy protein is present in the concentration of 10% weight. In another embodiment, glycerol is 35% w/w of the protein.

In yet another embodiment, the present invention provides a method for coating comestible product with an edible antimicrobial film solutions comprising mixing hydrocolloid in a range of 7.0 to 16.5 weight in water; adding glycerol of range of 0.63 to 1.5 weight; heating the mixture to a temperature between 60° to 85° C. thereby creating a solution; and applying the solution to comestible products. In another embodiment of the present method, the mixture is heated to 85° C. for 30 minutes.

Interestingly, a very thin coating of carboxylmethyl cellulose (8 µm) can be used without masking the color. Therefore, in another embodiment, the hydrocolloid is carboxylmethyl cellulose. In still another embodiment, the hydrocolloid is carboxylmethyl cellulose and the solution is applied to the comestible product at 8 µm.

The following examples are given for the purpose of illustrating various embodiments of the invention and are not meant to limit the present invention.

7. MATERIALS AND METHODS

7.1 Materials

Soy protein (SP) isolate (ARDEX) was obtained from Archer Daniel Midland (Decatur, Ill.). Whey protein (WP) isolate (PowerPro®) and wheat gluten (WG) were obtained from Land O'Lakes Food Ingredients Division (Arden Hills, Minn.) and Midwest Grain Products Inc. (Atchison, Kans.), respectively. Reagent grade alcohol (70%) was purchased from Fisher Chemical Company (Pittsburg, Pa.). Glycerol was purchased from Sigma Chemical Company (St. Louis, Mo.). Citric (anhydride EM), tartaric (EM), malic acid and lactic acids were purchases from EM Science (Gibbonstown, N.J.), J. T. Baker (Phillpsburg, N.J.) and Fisher Chemical Company (Pittsburg, Pa.), respectively. Nisin (Nisaplin) was obtained from Aplin & Barrett Ltd, Dorset, UK. Pathogenic bacteria *Listeria monocytogens*, *Salmonella gaminara* and *E. coli* 0157:H7 were obtained from Dr. M. G. Johnson's research laboratory, Department of Food Science, University of Arkansas, Fayetteville. Microbiological media, brain heart infusion (BHI) and nutrients agar (NA) were purchased from Difco Laboratories (Detroit, Mich.).

7.2 Methods 7.2.1 Concentrations of Polymer and Glycerol Used in Optimization of Film Forming Solutions 7.2.1.1 Soy Protein Film Soy protein (SP) isolate of 4 g, 6 g, 8 g, 10 g and 12 g per 100 g were used to optimize the concentration of SP in the film forming solutions. Optimal soy protein concentration was used to optimize glycerol concentration. Glycerol concentrations of 25%, 30%, 35%, 40% and 45% w/w of protein were used to optimize the concentration of plasticizer to the film forming solution.

SP isolate (4 g, 6 g, 8 g, 10 g and 12 g per 100 g) and de-ionized water (96 g, 94 g, 90 and 88 g per 100 g) were mixed and stirred for 30 minutes. Glycerol (25%, 30%, 35%, 40% and 45% w/w protein) was added to this mixture and stirred for 30 minutes. This mixture was heated to 85° C. for 30 minutes and stirred 15 minutes after the heating step. The film was cast on plastic sheet and dried in a humidity chamber at 60° C. with 45% relative humidity. After the film was peeled film, the thickness, color, puncture strength and water vapor permeability were determined (see FIG. 1).

7.2.1.2 Whey Protein Film

Whey protein (WP) of 4 g, 5 g, 6 g, 7 g, 8 g and 10 g per 100 g were used to optimize the concentration of WP in the film forming solutions. Optimized wheat protein concentration was used to optimize glycerol concentration. Glycerol concentrations of 25%, 30%, 35%, 40% and 45% w/w of protein were used to optimize the concentration of plasticizer to the film forming solution.

WP (4 g, 5 g, 6 g, 7 g, 8 g, 9 g and 10 per 100 g) and de-ionized water (96 g, 94 g, 90 g and 88 g per 100 g) were mixed and stirred for 30 minutes. Glycerol (25%, 30%, 35%, 40% and 45% w/w protein) was added to this mixture and stirred for 30 minutes. This mixture was heated to 85° C. for 10 minutes and stirred 15 minutes after the heating step. The film was cast on plastic sheet and dried in a humidity chamber at 60° C. with 45% relative humidity. The film was peeled off and the thickness, color, puncture strength and water vapor permeability were determined.

7.2.1.3 Wheat Gluten Film

Wheat gluten protein (WG) of 12 g, 14 g, 16 g and 18 g per 100 g were used to optimize the concentration of WP in the film forming solutions. Optimized wheat gluten concentration was used to optimize glycerol concentration. Glycerol concentrations of 25%, 30%, 35%, 40% and 45% w/w of protein were used to optimize the concentration of plasticizer to the film forming solution. Alcohol (70%) was used to dissolve WG.

WG (12 g, 14 g, 16 g and 18 g per 100 g) and de-ionized water (96 g, 94 g, 90 g and 88 g per 100 g) were mixed and stirred for 30 minutes. Glycerol (10%, 15%, 20%, 25%, 30%, 35%, 40% and 45% w/w protein) was added to this mixture and stirred for 30 minutes. This mixture was heated to 85° C. for 30 minutes and stirred 15 minutes after the heating step. The film was cast on plastic sheet and dried in a humidity chamber at 60° C. with 45% relative humidity. After the film was peeled off, the thickness, color, puncture strength and water vapor permeability were determined.

7.2.1.4 Carboxymethyl Cellulose Film

Carboxymethyl cellulose (CMC) of 1.0 g, 1.5 g and 2.0 g per 100 g were used to optimize the concentration of WP in the film forming solutions. Optimized wheat protein concentration was used to optimize glycerol concentration. Glycerol concentrations of 25%, 30%, 35%, 40% and 45% w/w of protein were used to optimize the concentration of plasticizer to the film forming solution.

CMC (1.0 g, 1.5 g and 2.0 g per 100 g) and de-ionized water (96 g, 94 g, 90 g and 88 g per 100 g) were mixed and stirred for 30 minutes. Glycerol (10%, 15%, 20%, 25%, 30%, 35%, 40% and 45% w/w protein) was added to this mixture and stirred for 30 minutes. This mixture was heated to 85° C. for 30 minutes and stirred 15 minutes after the heating step. The film was cast on plastic sheet and dried in a humidity chamber at 60° C. with 45% relative humidity. After the film was peeled off, the thickness, color, puncture strength and water vapor permeability were determined.

Figure 2:
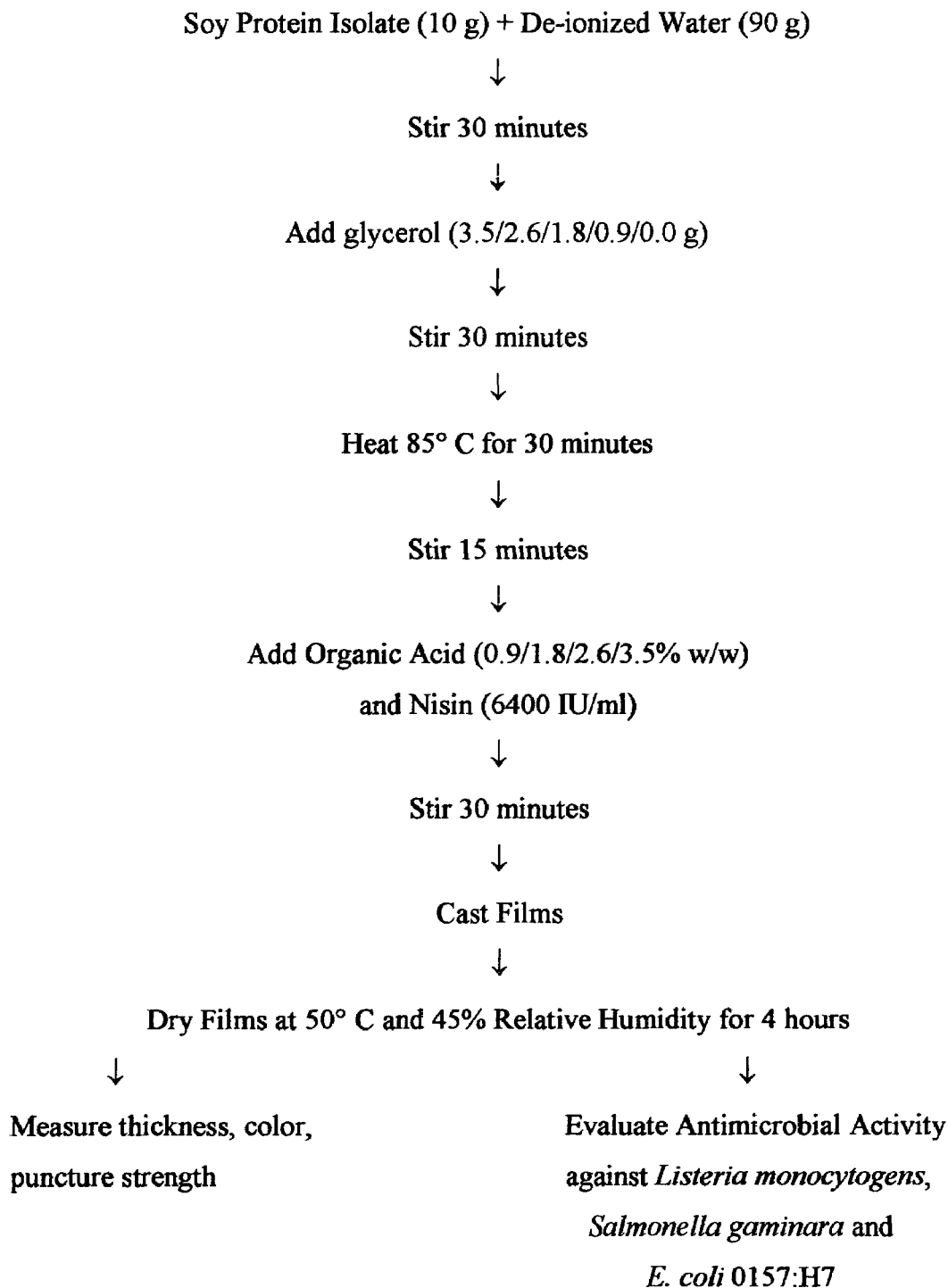
FIG. 2 is a schematic representation showing the steps for preparing soy protein film with organic acid incorporation.

7.2.2 Preparation of Soy Protein Film with Varying Concentration of Glycerol and Organic Acid Incorporation Ten grams of SP in fifty samples comprising citric, lactic, malic or tartaric at four levels with two duplicates; four controls at 4 different pHs with two duplicates and five samples without nisin with two duplicates were added to 90 g de-ionized water. The composition of organic acid added into the film forming solutions is shown in Table 2. Glycerol at 3.5; 2.6; 1.8; and 0.9 grams were added and homogeneously mixed by stirring with a magnetic bar for 30 min. The resulting solutions were heated at 85° C. for 30 min with stirring. After cooling to room temperature, nisin (6400 IU/ml) and/or citric, lactic, malic acid and tartaric acids (0; 0.9; 1.8; 2.6 g) were added to the heat treated film forming solution and stirred for 30 min (see FIG. 2). The pH of the control films were adjusted to 6.95 (original pH); 4.55; 3.85; and 3.35 using 2 N/0.2 N HCl. Control films without nisin and organic acids were used to evaluate the antimicrobial activity of organic and antimicrobial activity of nisin.

7.2.3 Film Casting

Fifty samples of film coating solutions produced as described above were cast onto 19×28 cm$^2$ silicone coated mylar plastic sheet (Richard Mistler, Inc., Morrisville, Pa.) by Draw-down equipment (Paul N. Gardner Company, Inc. Pompano Beach, Fla.) at uniform thickness and was dried in a humidity chamber (Hot Pack, Philadelphia, Pa.) at 50° C., 40% humidity for 4 hours. After drying, the films were removed from the plastic sheet and placed between wax paper and stored at ambient temperature and 50% relative humidity in a dry keeper (Sanplatec Corp. Japan).

7.2.4 Measurement of Thickness

Film thickness was measured with a micrometer (Model 2804-10, Mitutoyo, Japan) to the nearest 2.5 μm. Thickness was measured at four locations and averaged.

7.2.5 Measurement of Color

Film color was measured by a Minolta colorimeter CR-300 (USA) and recorded in CIE L*a*b* and L Chroma and Hue angle. The L*a*b* color system consist of a luminance or lightness component (L*) and two chromatic components: the a* component for green (−a) to red (+a) and the b* component from blue (−b) to yellow (+b) colors. In L*C H° system L* represents lightness C* represents chroma and H represents Hue angle. Film samples were placed under white standard plate and color L*a*b* and L*C*H° values were measured. Four pieces were measured three times for each sample and averaged.

7.2.6 Measurement of Puncture Strength

Puncture strength of the films was measured using a texture analyzer (TA-XT2I, Texture Technologies Corp., NY). Film samples were conditioned at room temperature and 60% relative humidity at least 48 hours before testing. Puncture strength was measured by mounting 30 mm film piece on 10 mm film testing rig (TA-108S Mini) and puncturing with a 2 mm probe (TA-52). The force (N) at the point of rupture was recorded as puncture strength.

7.2.7 Preparation of Bacterial Suspension

The effect of citric, lactic, malic and tartaric acids on antimicrobial activity of nisin (6400 IU/g protein) incorporated soy protein film against *Listeria monocytogens, Salmonella gaminara* and *E. coli* 0157:H7 was studied. Frozen stocks (at −80° C.) of *Listeria monocytogens, Salmonella gaminara* and *E. coli* 0157:H7 were transferred to 10 ml brain heart infusion (BHI) broth by a sterile inoculation loop and incubated at 37° C. for 24 hours. On the second day, 10 μl of the bacterial suspension was transferred to 10 ml BHI broth and incubated at 37° C. for 18 hours.

7.2.8 Antibacterial Effectiveness of Film Disc (Clear Inhibition Zone Assay)

Soft agar was prepared by mixing 0.8 g nutrient agar with 100 ml de-ionized water. After boiling, 10 ml soft agar solutions was dispensed into test tubes. Sterilization of soft agar tubes was performed by autoclaving. Prior to using, the soft agar tubes were melted by placing the tubes in a boiling water bath and cooled to 37° C. Ten microliters of bacterial culture (total 10$^6$ cfu) in BHI broth from second day culture was mixed with 10 ml of soft agar (0.8% nutrient agar) at 37° C. and overlaid onto nutrient agar plate. Circular film discs (1-cm diameter) were placed on soft agar after setting. Plates were incubated 37° C. for 24 hours and the clear zone in the bacterial lawn was visually examined and the thickness of the clear zone was recorded.

7.2.9 Plate Count of Bacterial Survivors

The bacterial suspension of second day culture (∼10$^8$∼10$^9$ CFU/ml) was 10 fold diluted by using phosphate buffer (pH 7) and 1.5 μl (total 1.5×10$^6$ bacteria) of the diluted suspension was inoculated into film disc. After the pre-inoculated film disc was transferred to stomacher bag, 985 μl phosphate buffer solution was added and stomached for 2 min. Dissolved film suspension was serially diluted up to 10$^4$ times by using phosphate buffer (pH 7) and spread plated onto nutrient agar plates. Plates were incubated at 37° C. for 24 hours and colonies counted. Log reduction was calculated by the following equation:

Log reduction=Log number of CFU/ml in control without film−Log number of CFU/ml in film samples.

7.2.10 Preparation of Soy Protein Coating Solution

Figure 3:
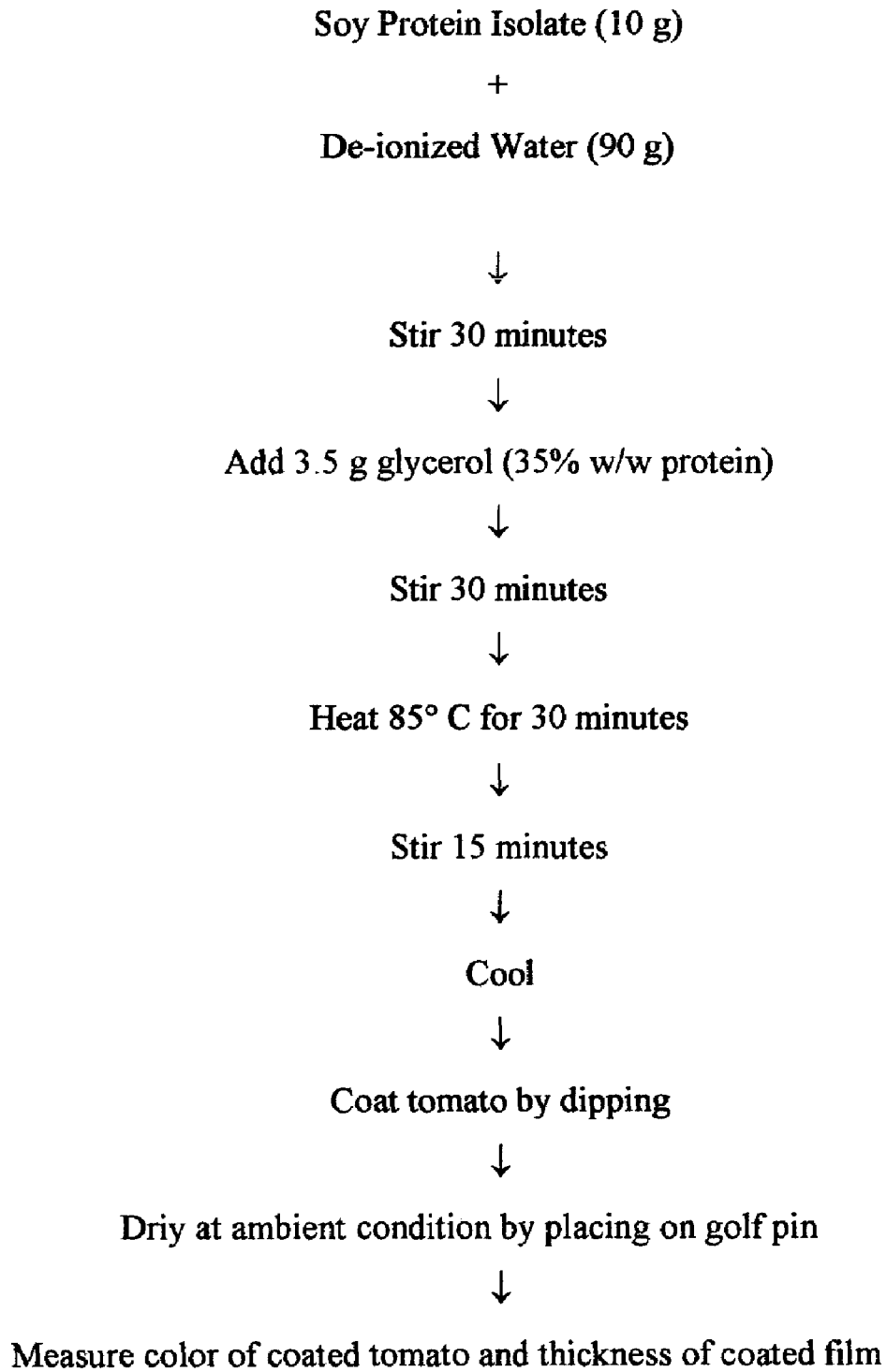
FIG. 3 is a schematic representation showing the steps for preparing soy protein coating solution.
Figure 4:
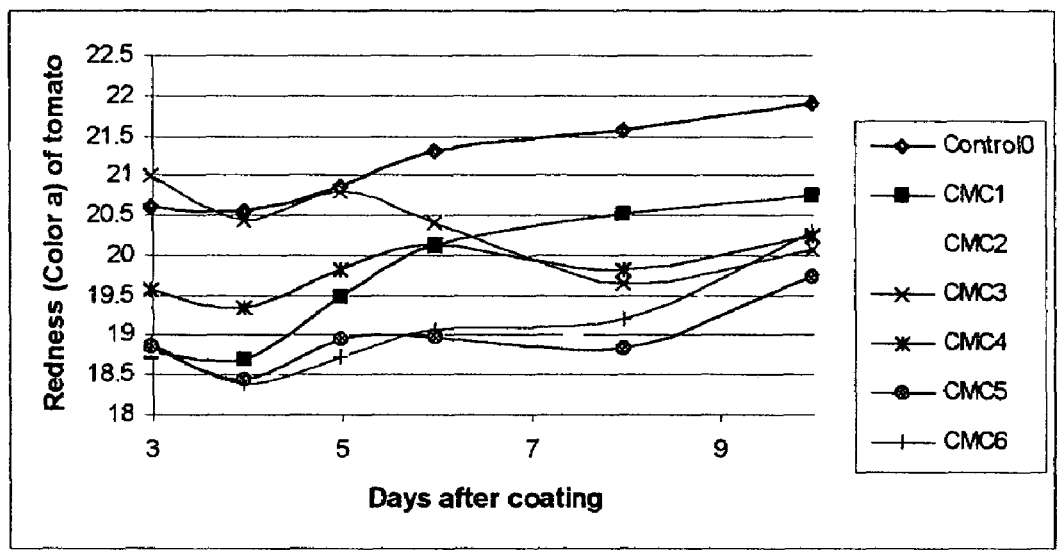
FIG. 4 is a graph showing the effects of 1 to 6 carboxymethyl cellulose film coatings on the redness of tomato during storage.
Figure 5:
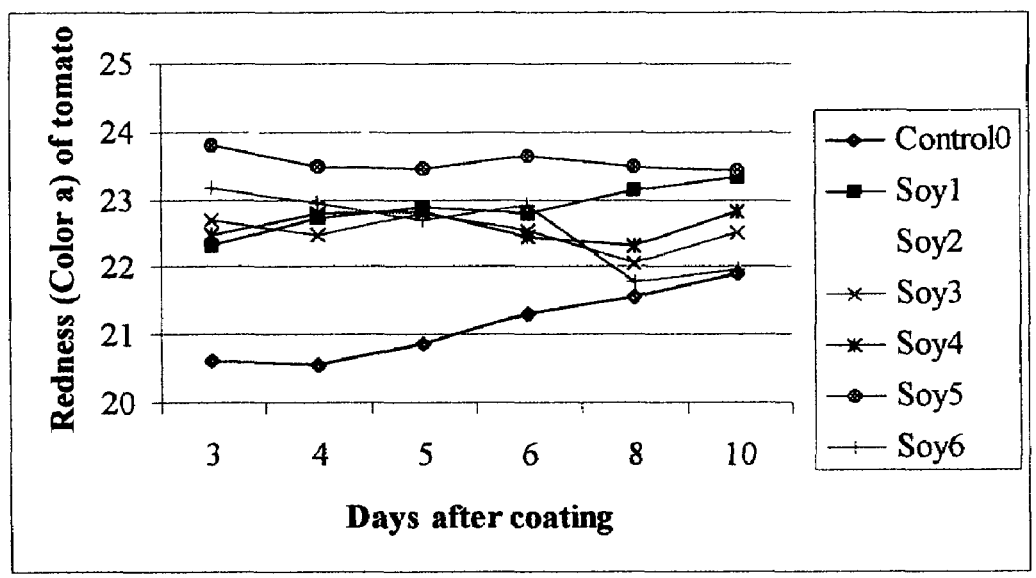
FIG. 5 is a graph showing the effects of 1 to 6 soy protein film coatings on the redness of tomato during storage.
Figure 6:
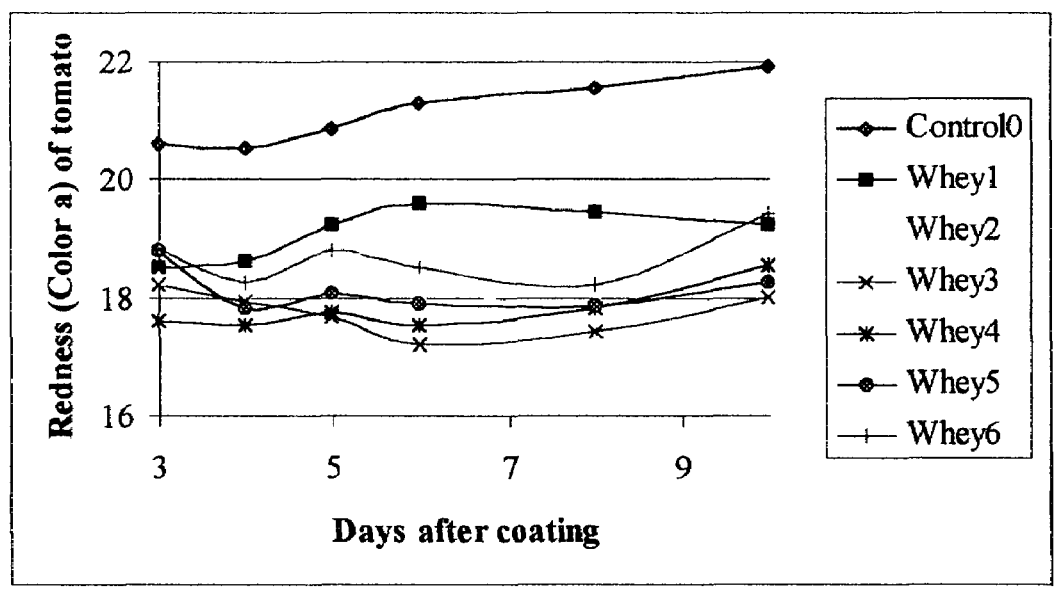
FIG. 6 is a graph showing the effects of 1 to 6 whey protein film coatings on the redness of tomato during storage.
Figure 7:
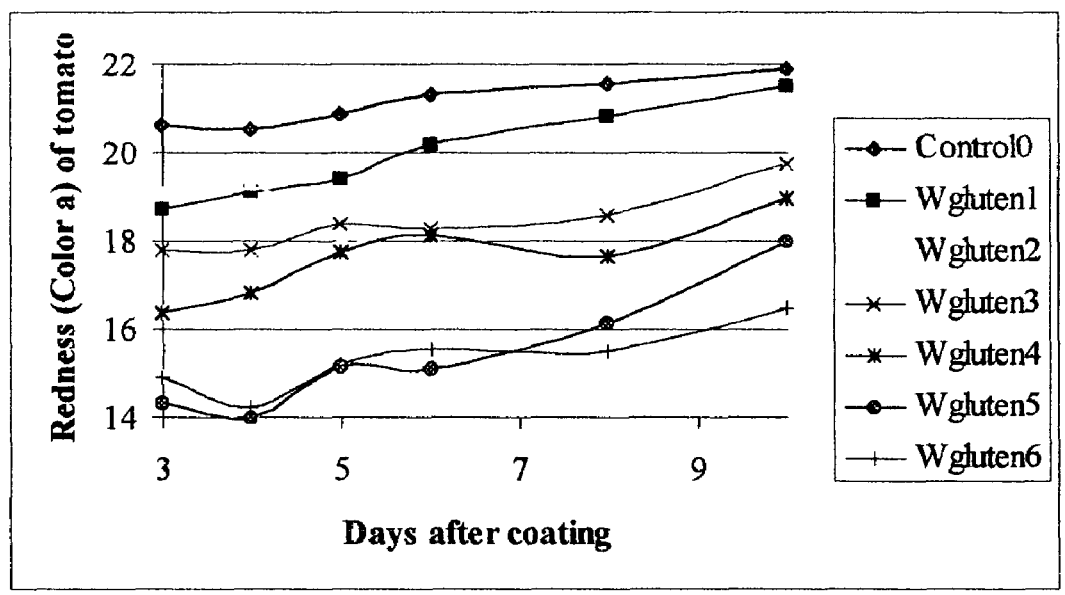
FIG. 7 is a graph showing the effects of 1 to 6 wheat gluten film coatings on the redness of tomato during storage.

Ten grams of SP was mixed with 90 g de-ionized water and stirred for 30 minutes. Glycerol (3.5 g) was added to the mixture and stirred for another 30 minutes. The resulting solution was heated at 85° C. for 30 minutes and stirred another 15 minutes. After cooling to room temperature, tomatoes were dipped in the solution. The tomatoes were dried at ambient condition by placing on golf pins. The color of the coated tomato and thickness of the coated film were measured. (see FIG. 3).

7.2.11 Preparation of Whey Protein Coating Solution

Seven grams of whey protein was mixed with 93 g de-ionized water and stirred for 30 minutes. Glycerol (2.45 g) was added to the mixture and stirred for another 30 minutes. The resulting solution was heated at 85° C. for 10 minutes and stirred another 15 minutes. After cooling to room temperature, tomatoes were dipped in the solution. The tomatoes were dried at ambient condition by placing on golf pins. The color of the coated tomato and thickness of the coated film were measured.

7.2.12 Preparation of Wheat Gluten Coating Solution 16.5 grams of wheat gluten protein was dissolved in 70% reagent alcohol and mixed with 83.5 g de-ionized water and stirred for 30 minutes. Glycerol (2.8 g) was added to the mixture and stirred for another 30 minutes. The resulting solution was heated at 85° C. for 15 minutes and stirred another 15 minutes. After cooling to room temperature, tomatoes were dipped in the solution. The tomatoes were dried at ambient condition by placing on golf pins. The color of the coated tomato and thickness of the coated film were measured.

7.2.13 Preparation of Carboxymethyl Cellulose Coating Solution 1.5 grams of SP was mixed with 98.5 g de-ionized water and stirred for 30 minutes. Glycerol (0.5 g) was added to the mixture and stirred for another 30 minutes. The resulting solution was heated at 85° C. for 30 minutes and stirred another 15 minutes. After cooling to room temperature, tomatoes were dipped in the solution. The tomatoes were dried at ambient condition by placing on golf pins. The color of the coated tomato and thickness of the coated film were measured.

7.2.14 Preparation of Tomato Coating

Tomatoes were coated with soy protein, whey gluten protein, wheat protein and carboxymethyl cellulose film-solutions. Seventy-two (72) tomatoes were washed to remove foreign materials and dried at ambient condition. Eighteen (18) tomatoes were dipped into three replicate film-forming solution for each polymer and dried on golf pins. After drying, one tomato from each replicate film-forming solution for each polymer was peeled and measured for thickness after one coating. The thickness was measured at four locations and averaged. The remaining fifteen (15) tomatoes were coated again ($2^{nd}$ coating) with each polymer and placed on golf pins to dry. After drying, one tomato from each replicate of the $2^{nd}$ coating was peeled and measured ofr thickness with a micrometer (Model 2804-10, Mitutoyo, Japan) to the nearest 2.5 μm. The remaining twelve (12) tomatoes were coated again ($3^{rd}$ coating) with each polymer and placed on golf pins to dry. This procedure was repeated up to 6 coatings to obtain coated film at different thickness.

7.2.15 Measurement of Tomato Coating

Ninety (90) tomatoes were washed and dried. Eighteen (18) tomatoes were dipped into three replicate film-forming solution for each polymer and placed on golf pins to dry. Eighteen tomatoes were used as control (without coating) to measure the color changes of tomato with time. After drying, the color L*a*b* Chroma and hue angle of the tomatoes were measured using a Minolta colorimeter CR-300 ((Minolta Co., Ltd, Ramsey, N.J.). The remaining fifteen (15) tomatoes were coated again ($2^{nd}$ coating), dried and measured for color. L*a*b* Chroma and hue angle. After each coating and drying, color measurements were taken at the same position. This procedure was repeated for 6 coatings.

Control tomatoes (non-coated) and coated tomatoes were measured at the same time. Coated and non-coated tomatoes were kept at room temperature for 10 days and color measurements were taken every day.

7.2.16 Statistical Analysis

All experiments were performed in duplicates. Data was analyzed by a generalized liner model (GLM) of SAS Institute (Cary, N.C.). The Duncan's Multiple Range Test was used to compare differences in means of treatment (SAS Institute, Inc. 1992).

The tomato color after 1 to 6 coatings and during storage up to 10 days was analyzed by general liner model (GLM) of SAS Institute, Inc. (Cary, N.C.). The initial tomato color was used as covariance and adjusted means was used to compare differences between means of treatments and control by Dunnet's test (SAS Institute, Inc. 1992).

8. EXAMPLES

8.1 Example I

Optimum Concentrations of Polymer and Glycerol Used to Produce Optimum Film Forming Solutions Table 1 shows the concentrations of soy, whey, wheat protein and CMC isolate used to optimize the film forming solutions. Optimum concentrations of soy, whey, wheat proteins and carboxymethyl cellulose to produce homogenous films were 10 g; 7 g; 16.5 g; 1.5 g per 100 g respectively. Optimum concentrations of glycerol to produce films with elasticity and mechanical strength were 30%; 35%; 15%; 15% w/w of soy, whey, wheat, wheat protein and carboxymethyl cellulose, respectively. Soy protein concentrations of 4.0; 6.0; and 8.0 g per 100 g resulted in running of the film solution out of plastic sheet during drying while protein concentration, 12.0 g per 100 g, resulted in the formation of a thicker gel, and did not spread homogeneously.

Soy protein concentration of 10 g per 100 g was selected to optimize the glycerol concentration. The optimum concentration of glycerol required to produce soy protein film was 30% (w/w protein). Glycerol concentrations below 30% produced brittle soy protein films.

Whey protein concentrations of 4.0, 5.0 and 6.0 g per 100 g resulted in running of the film solutions out of plastic sheet during drying while protein concentrations of 8.0, and 9.0, 10 per 100 g resulted in formation of a thicker gel and non-homogenous spread. Whey protein concentration of 7 g per 100 g was selected to optimize the glycerol concentration. The optimum concentration of glycerol required to produce whey protein film was 35% (w/w protein). Glycerol concentrations below 35% produced brittle whey protein films.

Wheat gluten concentrations of 12.0, 14.0 and 16.0 g per 100 g resulted in running of the film solution out of plastic sheet during drying while protein concentrations of 17.0, 17.5 and 18.0 g per 100 g resulted in the formation of clump and thickening of gel and a non-homogenous spread. Wheat gluten concentration of 16.5g per 100 g was selected to optimize the glycerol concentration. The optimum concen-

TABLE 1

Concentration of polymer and glycerol used in optimization of film forming solutions preparation and their optimized concentrations

| Polymer | Polymer concentrations used in optimization (g/100 g) | Optimum polymer concentration (g/100 g) | Glycerol concentrations used in optimization (% w/w of polymer) | Optimum glycerol concentration (% w/w of polymer) |
|---|---|---|---|---|
| Soy protein | 4.0, 6.0, 8.0, 10.0, 12.0 | 10.0 | 25, 30, 35, 40, 45 | 30 |
| Whey protein | 4.0, 5.0, 6.0, 7.0, 8.0, 9.0, 10.0 | 7.0 | 25, 30, 35, 40, 45 | 35 |
| Wheat gluten | 12.0, 14.0, 16.0, 16.5, 17.0, 17.5, 18.0 | 16.5 | 10, 15, 20, 25, 30, 35, 40, 45 | 15 |
| Carboxymethyl cellulose | 1.0, 1.5, 2.5 | 1.5 | 10,, 15, 20, 25, 30, 35, 40, 45 | 15 | tration of glycerol required to produce wheat gluten film was 15% (w/w protein). Glycerol concentrations below 15% produced brittle wheat gluten films.

Carboxymethyl cellulose concentrations of 1.0 g per 100 g resulted in a non-continuous film while a concentration of 2.0 g per 100 g resulted in the formation of a thicker film solution and a non-homogenous spread. A concentration of 1.5 g per 100 g of carboxymethyl cellulose was selected to optimize the glycerol concentration. The optimum concentration of glycerol required to produce carboxymethyl cellulose films was 15% (w/w carboxymethyl cellulose). Glycerol concentrations below 15% produced brittle cellulose films.

8.2 Example II

Preparation of Organic Acid Incorporated Soy Protein Film

Optimized soy protein film was selected to study the effect of citric, lactic, malic and tartaric acids on mechanical property of nisin (6400 IU/g) incorporated film. Soy protein was selected because of its suitability to produce films at a wide range of pH and additives without any adverse effect on solubility. Antimicrobial nisin was selected at a level of 6400 IU/g that would not cause complete destruction of microorganisms. Since organic acids have OH groups in their molecules, plasticizing effect of organic acid in combination with glycerol was investigated. Glycerol percentages of 25, 50 and 75 were replaced with organic acid percentages of 75, 50 and 25. The glycerol used to produce desirable film was 3.5 g in the films forming solutions. Control films with 3.5 g of glycerol were also included. Films produced with 3.5 g of organic acid and 0 g glycerol were brittle.

Soy protein isolate, de-ionized water and glycerol were mixed in the amounts shown in Table 2. The resulting solution was heated at 85° C. for 30 min with stirring. Nisin (6400 IU/ml) and/or citric, lactic, malic and tartaric acids (0; 0.9; 1.8; and 2.6 g) was added to the heat treated film forming solution and stirred for 2 hours. Control films without nisin were produced to evaluate the antimicrobial activity of organic acids. Control films without organic acids were produced to evaluate the antimicrobial activity of nisin.

TABLE 2

Compositions of organic acid incorporated film forming solutions

| Treatment | Soy proteins (g) | De-ionized water (g) | Glycerol (g) | Organic acid (citric/lactic/malic/tartaric) (g) |
|---|---|---|---|---|
| 1 | 10.0 | 90.0 | 3.5 | 0 |
| 2 | 10.0 | 90.0 | 2.6 | 0.9 |
| 3 | 10.0 | 90.0 | 1.8 | 1.8 |
| 4 | 10.0 | 90.0 | 0.9 | 2.6 |
| 5 | 10.0 | 90.0 | 2.6 | 2.6 |
| 6 | 10.0 | 90.0 | 0 | 3.5 |

8.3 Example III

Thickness and Puncture Strength

Table 3 shows the effect of organic acids, nisin and glycerol on the thickness and puncture strength of the soy protein film. Thickness of citric (38.4 to 44.7 μm) and tartaric (34.9 to 42.6 μm) acids incorporated film were higher than lactic (23.8 to 38.7 μm) and malic (21.3 to 32.7 μm) acids incorporated film. Higher molecular weight (192.13 Dalton) of citric acid and tartaric (150.09 Dalton) compared to malic (134.09 Dalton) and lactic (90.08 Dalton) acids may account for this increase in thickness of the film.

Since the mechanical strength of the film was low, puncture strength was measured to evaluate mechanical strength of the film. The addition of nisin and lowering of the pH from 6.95 (original pH) to 4.55 and 3.85 (near isoelectric pH) decreased the puncture strength of the soy protein film. This is in agreement with previous reports that puncture strength of soy protein film was lower in acidic pH and higher in alkaline pH (Rhim et al., 2000). Other reports suggested that the incorporation of nisin increased the puncture strength of SP film from 5.36N to 7.22N (Ko et al., 2001). This may be due to the higher thickness of the film with nisin (169 μm) than without nisin (156.4 μm). In the present invention, the puncture strength of nisin incorporated films was lower than films without nisin. Lower molecular weight components decrease interaction between protein molecules and reduce puncture strength of the film.

Increasing amount citric, lactic and malic acid from 0.9 to 2.6% revealed no effect on the mechanical strength of the film. Moreover, tartaric acid lowered the puncture strength (0.16 to 1.33N) of the film compared to the control (0.32 to 0.62N). This may be due to reduction in protein-protein interaction by linear tartaric acid molecules (HOOC—CHOH—CHOH—COOH). Film samples containing 2.6% glycerol and 2.6% citric, lactic and malic acids demonstrated high puncture strength (0.90; 0.87; 0.97N, respectively) compared to samples containing low glycerol and organic acid (0.16 to 0.62N). One possibility is that films containing 2.6% citric, lactic or malic acids may cross link with the unfolded protein molecules and glycerol may reduce interchain attractive forces and increase flexibility of protein molecule.

TABLE 3

Effects of partial replacement of glycerol plasticizer with citric, lactic, malic and tartaric acids, on pH, thickness and puncture strength soy protein film

| Acid Types (g/100 g) | Glycerol (g/100 g) | Nisin IU protein | pH | Thickness (um) | Puncture Strength (N) |
|---|---|---|---|---|---|
| Original pH 6.95 | 3.5 | 6400 | 6.95 | 27.3$^{fghi}$ | 0.42$^{cdefg}$ |
| Hydrochloric pH 4.55 | | 6400 | 4.55 | 31.4$^{defghi}$ | 0.32$^{fghij}$ |
| Hydrochloric pH 3.85 | 3.5 | 6400 | 3.85 | 29.2$^{efghi}$ | 0.34$^{efghi}$ |
| Hydrochloric pH 3.35 | 3.5 | 6400 | 3.35 | 20.8$^{i}$ | 0.35$^{efghi}$ |
| Hydrochloric pH 3.35 | 3.5 | 0 | 3.36 | 33.3$^{bcdefgh}$ | 0.62$^{b}$ |
| Citric (0.9) | 2.6 | 6400 | 4.39 | 44.1$^{ab}$ | 0.46$^{cde}$ |
| Citric (1.8) | 1.8 | 6400 | 3.72 | 44.7$^{a}$ | 0.29$^{ghij}$ |
| Citric (2.6) | 0.9 | 6400 | 3.35 | 38.4$^{abcde}$ | 0.20$^{jk}$ |
| Citric (2.6) | 0.9 | 0 | 3.32 | 41.2$^{abcd}$ | 0.26$^{ijk}$ |
| Citric (2.6) | 2.6 | 6400 | 3.32 | 35.6$^{ab}$ | 0.90$^{a}$ |
| Lactic (0.9) | 2.6 | 6400 | 4.55 | 38.7$^{abcde}$ | 0.45$^{cdef}$ |
| Lactic (1.8) | 1.8 | 6400 | 3.85 | 35.6$^{abcdefg}$ | 0.56$^{bc}$ |
| Lactic (2.6) | 0.9 | 6400 | 3.41 | 23.8$^{hi}$ | 0.35$^{efghi}$ |
| Lactic (2.6) | 0.9 | 0 | 3.45 | 29.9$^{efghi}$ | 0.28$^{hijk}$ |
| Lactic (2.6) | 2.6 | 6400 | 3.47 | 29.5$^{efghi}$ | 0.87$^{a}$ |
| Malic (0.9) | 2.6 | 6400 | 4.25 | 35.6$^{ab}$ | 0.41$^{defgh}$ |
| Malic (1.8) | 1.8 | 6400 | 3.65 | 32.7$^{cdefgh}$ | 0.49$^{cd}$ |
| Malic (2.6) | 0.9 | 6400 | 3.34 | 21.31$^{i}$ | 0.30$^{ghij}$ |
| Malic (2.6) | 0.9 | 0 | 3.29 | 30.2$^{efghi}$ | 0.46$^{cdef}$ |
| Malic (2.6) | 2.6 | 6400 | 3.23 | 25.7$^{ghi}$ | 0.97$^{a}$ |
| Tartaric (0.9) | 2.6 | 6400 | 4.05 | 42.6$^{abc}$ | 0.33$^{efghij}$ |
| Tartaric (1.8) | 1.8 | 6400 | 3.34 | 38.1$^{abcdefg}$ | 0.23$^{ijk}$ |
| Tartaric (2.6) | 0.9 | 6400 | 3.05 | 35.2$^{abcdefg}$ | 0.16$^{k}$ |

TABLE 3-continued

Effects of partial replacement of glycerol plasticizer with citric, lactic, malic and tartaric acids, on pH, thickness and puncture strength soy protein film

| Acid Types (g/100 g) | Glycerol (g/100 g) | Nisin IU/g protein | pH | Thickness (um) | Puncture Strength (N) |
|---|---|---|---|---|---|
| Tartaric (2.6) | 0.9 | 0 | 3.00 | 37.5$^{abcdefg}$ | 0.16$^k$ |
| Tartaric (2.6) | 2.6 | 6400 | 3.00 | 34.9$^{abcdefg}$ | 0.41$^{defgh}$ |

$^{abcdefghijkl}$are indicators of statistical differences among values. Superscripts "a" or "l" indicate that the values decrease from "a" to "l". The use of the same superscript in a column means, two values are not statistically different although they are numerically different.

8.4 Example IV

Zone of Inhibition

Antimicrobial activity of the film was measured by 1 cm-diameter film disk on lawn of *Listeria monocytogens, Salmonella gaminara* and *E. coli* 0157:H7 containing nutrients agar plate. Thickness of the clear zone around the film disk in the lawn of bacteria is shown on Table 3. Very little inhibition of *L. monocytogens* (<0.1 mm) was observed in soy protein film containing nisin and 3.5% glycerol. However, inhibition of *L. monocytogens* increased in the presence of 0.9; 1.8 and 2.6% of citric acid (1.6, 2.4 and 4.0 mm), malic acid (1.5, 3.0 and 5.5 mm) and tartaric acid (2.0, 3.5 and 4.8 mm) compared to control (without organic acid) at pH 4.55, 3.85 and 3.35 (<0.5, 1.0 and 1.5 mm). Films with 2.7% organic acids without nisin also demonstrated the same level of inhibition as with nisin. *Salmonella* was inhibited only by the incorporation of citric acid 2.6% (<0.1 and 1.1 mm). Films with 2.6% organic acids without nisin revealed lower levels of anti-*salmonella* activity. *E. coli* 0157:H7 was also inhibited by incorporation of citric acid 1.8 and 2.6% (<0.2 and 1.0 mm), malic acid 2.6% (1.5 mm) and tartaric acid 1.8 and 2.6% (<0.8 and 1.99 mm). Lactic acid (2.6%) demonstrated the least effect on anti-*salmonella* (0.1 mm) and anti-*E. coli* 0157:H7% (0.1 mm) activities. However, 2.6% glycerol and 2.6% lactic acid showed higher levels of anti-salmonella (0.5 mm) and anti-EHEC (0.5 mm) activities.

TABLE 4

Effects of citric, lactic, malic and tartaric acids containing soy protein film on log reduction of *Listeria monocytogens, Salmonella gaminara* and *E. coil* 0157:H7.

| Treatment | | | Log Reduction | | |
|---|---|---|---|---|---|
| Acid Types (%) | Glycerol (%) | Nisin IU/g protein | Listeria mono- cytogens | Salmonella gaminara | E. coli 0157:H7 |
| Hydrochloric | 3.5 | 6400 | −0.18$^{cdefg}$ | −0.03$^g$ | 0.06$^{cd}$ |
| Citric (0.9) | 2.6 | 6400 | −0.67$^{fg}$ | 0.57$^{fg}$ | −0.98$^{ef}$ |
| Citric (1.8) | 1.8 | 6400 | 0.49$^{bcd}$ | 0.64$^{efg}$ | −0.87$^{ef}$ |
| Citric (2.6) | 0.9 | 6400 | −0.11$^{bcdefg}$ | 0.72$^{efg}$ | 0.41$^{cd}$ |
| Citric (2.6) | 0.9 | 0 | −0.26$^{cdefg}$ | 0.99$^{efg}$ | 0.46$^{cd}$ |
| Citric (2.6) | 2.6 | 6400 | 0.10$^{bcdefg}$ | 0.77$^{efg}$ | 0.45$^{cd}$ |
| Lactic (0.9) | 2.6 | 6400 | −0.76$^g$ | 0.30$^{fg}$ | 0.16$^d$ |
| Lactic (1.8) | 1.8 | 6400 | −0.13$^{bcdefg}$ | 1.43$^{efg}$ | 0.22$^d$ |
| Lactic (2.6) | 0.9 | 6400 | 0.53$^{bc}$ | 7.37$^b$ | 1.29$^b$ |
| Lactic (2.6) | 0.9 | 0 | 0.79$^b$ | 6.34$^b$ | 0.73$^{bcd}$ |
| Lactic (2.6) | 2.6 | 6400 | 0.19$^{cdefg}$ | 8.77$^d$ | 0.90$^{bc}$ |
| Malic (0.9) | 2.6 | 6400 | −0.43$^{defg}$ | 0.23$^{fg}$ | −0.53e |
| Malic (1.8) | 1.8 | 6400 | −0.48$^{efg}$ | 1.68$^{def}$ | −0.55e |

TABLE 4-continued

Effects of citric, lactic, malic and tartaric acids containing soy protein film on log reduction of *Listeria monocytogens, Salmonella gaminara* and *E. coil* 0157:H7.

| Treatment | | | Log Reduction | | |
|---|---|---|---|---|---|
| Acid Types (%) | Glycerol (%) | Nisin IU/g protein | Listeria mono- cytogens | Salmonella gaminara | E. coli 0157:H7 |
| Malic (2.6) | 0.9 | 6400 | 0.64$^{bc}$ | 4.32$^c$ | 0.75$^{bcd}$ |
| Malic (2.6) | 0.9 | 0 | 2.48$^a$ | 7.52$^{ab}$ | 2.28$^a$ |
| Malic (2.6) | 2.6 | 6400 | 0.47$^{bcd}$ | 4.76$^c$ | 0.42$^{cd}$ |
| Tartaric (0.9) | 2.6 | 6400 | 0.14$^{bcdefg}$ | 0.36$^{fg}$ | −0.66$^e$ |
| Tartaric (1.8) | 1.8 | 6400 | 0.38$^{bcde}$ | 0.46$^{fg}$ | −1.29$^f$ |
| Tartaric (2.6) | 0.9 | 6400 | 0.14$^{bcdefg}$ | 2.06$^{de}$ | 0.45$^{cd}$ |
| Tartaric (2.6) | 0.9 | 0 | −0.03$^{bcdefg}$ | 4.47$^c$ | 0.48$^{cd}$ |
| Tartaric (2.6) | 2.6 | 6400 | 0.14$^{bcdefg}$ | 2.92$^d$ | 0.26$^c$ |

TABLE 5

Effects of citric, lactic, malic and tartaric acids incorporated soy protein film on the log number of *Listeria monocytogens, Salmonella gaminara* and *E. coli* 0157:H7.

| Treatment | | | Log Number | | |
|---|---|---|---|---|---|
| Acid Types (%) | Glycerol (%) | Nisin IU/g protein | Listeria mono- cytogens | Salmonella gaminara | E. coli 0157:H7 |
| Hydrochloric | 3.5 | 6400 | 8.16$^a$ | 8.73$^a$ | 7.98$^{cdef}$ |
| Citric (0.9) | 2.6 | 6400 | 8.44$^{cd}$ | 7.87$^{abc}$ | 8.88$^{ab}$ |
| Citric (1.8) | 1.8 | 6400 | 7.29$^{cd}$ | 7.75$^{abc}$ | 8.77$^{ab}$ |
| Citric (2.6) | 0.9 | 6400 | 7.88$^{bcd}$ | 8.02$^{abc}$ | 8.12$^{cdef}$ |
| Citric (2.6) | 0.9 | 0 | 8.24$^{ab}$ | 7.75$^{abc}$ | 8.07$^{cdef}$ |
| Citric (2.6) | 2.6 | 6400 | 7.71$^{abcd}$ | 7.98$^{abc}$ | 8.07$^{cdef}$ |
| Lactic (0.9) | 2.6 | 6400 | 8.53a | 8.25$^{ab}$ | 7.75efg |
| Lactic (1.8) | 1.8 | 6400 | 7.90$^{abcd}$ | 7.12$^{bcd}$ | 7.68$^{fg}$ |
| Lactic (2.6) | 0.9 | 6400 | 7.46$^{bcd}$ | 1.27$^{fg}$ | 7.30$^g$ |
| Lactic (2.6) | 0.9 | 0 | 7.19$^d$ | 2.40$^f$ | 7.86$^{defg}$ |
| Lactic (2.6) | 2.6 | 6400 | 7.61$^{abcd}$ | 0.00$^g$ | 7.69$^{fg}$ |
| Malic (0.9) | 2.6 | 6400 | 8.20$^{abc}$ | 8.33$^{ab}$ | 8.43$^{bcd}$ |
| Malic (1.8) | 1.8 | 6400 | 8.25$^{ab}$ | 6.87$^{bcd}$ | 8.45$^{bcd}$ |
| Malic (2.6) | 0.9 | 6400 | 7.34$^{bcd}$ | 4.42$^e$ | 7.77$^{efg}$ |
| Malic (2.6) | 0.9 | 0 | 5.51$^e$ | 1.23$^{fg}$ | 6.25$^h$ |
| Malic (2.6) | 2.6 | 6400 | 7.33$^{bcd}$ | 4.01$^e$ | 8.10$^{cdef}$ |
| Tartaric (0.9) | 2.6 | 6400 | 7.64$^{abcd}$ | 8.19$^{ab}$ | 8.55$^{bc}$ |
| Tartaric (1.8) | 1.8 | 6400 | 7.40$^{bcd}$ | 8.10$^{ab}$ | 9.19$^a$ |
| Tartaric (2.6) | 0.9 | 6400 | 7.84$^{abc}$ | 6.57$^{cd}$ | 8.14$^a$ |
| Tartaric (2.6) | 0.9 | 0 | 8.01$^{abcd}$ | 4.32$^e$ | 8.11$^{cdef}$ |
| Tartaric (2.6) | 2.6 | 6400 | 7.67$^{abcd}$ | 5.82$^d$ | 8.33$^{bcde}$ |

Tables 4 and 5 show the effectiveness of organic acid, nisin and glycerol incorporation on the log number and log reduction of *Listeria monocytogens, Salmonella gaminara* and *E. coli* 0157:H7 inoculated soy protein film. *Salmonella gaminara* is more susceptible to organic acid than *Listeria monocytogens* and *E. coli* 0157:H7. *Salmonella gaminara* is more susceptible to 2.6% malic acid, lactic and tartaric acids without nisin (1.23, 2.40 and 4.32 log numbers and 7.52, 6.34 and 4.47 log reduction respectively). Previous reports revealed log reductions of 2.03, 1.63 and 0.91 for *Listeria monocytogens, Salmonella gaminara* and *E. coli* 0157:H7, respectively, when lean beef tissue was treated with 1.7% lactic acid and stored at 5° C. for 7 days (Sirugusa and Diuckson, 1993). In the present invention, 2.6% lactic acid caused 0.79, 8.77 and 1.29 log reductions of *Listeria monocytogens, Salmonella gaminara* and *E. coli* 0157:H7.

Incorporation of nisin (6400 IU/g protein) did not influence the susceptibility of *Salmonella gaminara* to lactic acid (7.37 log reduction) but decreased susceptibility to malic and tartaric acids (4.32 and 2.06 log reduction respectively). *Listeria monocytogens* and *E. coli* 0157:H7 were more susceptible to malic acid (2.6%) without nisin (2.48 and 2.28 log reductions, respectively). However, incorporation of nisin decreased the susceptibility of *Listeria monocytogens* and *E. coli* 0157:H7 to malic acid (0.64 and 0.75 log reductions, respectively). Tartaric acid showed no effect on the inhibition of *Listeria monocytogens* and *E. coli* 0157:H7. Citric acid showed marginal effect against *S. gaminara* and no effect against *Listeria monocytogens* and *E. coli* 0157:H7. Prior reports demonstrated that lactic acid was more effective than citric acid in inhibiting *Salmonella enteritidis* and *E. coli* (Richards et al., 1995). Others reported that at low concentrations (0.2 and 0.4%) citric acid did not snow any significant reduction of *Salmonella montevideo* on the surface or core tissue of tomatoes coated with cellulose based edible film (2.18 and 1.92 log reductions) (Zhuang et al., 1996). Yet, another report revealed that 3.2% of commercial washing formulations for fruits and vegetables containing citric acid and surfactant at pH 2.3 caused 2.1 log reductions of *E. coli* (ATCC 25922) on apple halves (Sapers et al., 1999). While, Shelet reported a 4.84 log reduction in *Salmonella typhimurum* contaminated in broiler drum stick skin treated with nisin (100 mg/ml), citric acid (3.27%) and Tween 20 (0.61%) at pH 3.5 (Shelet et al., 1995). One report demonstrated less than one log reduction in *Listeria monocytogens* counts up to 5 days in 2% citric, hydrochloric, lactic, malic and tartaric acid rinsed catfish fillets stored at 4° C. (Farid et al., 1998). Therefore, incorporation of malic and lactic acid into soy protein films improves the antimicrobial activity of organic acid.

The results shown in Table 2 demonstrate that plasticizer glycerol (2.7% of 3.5% w/v) can be partially replaced with organic acid (2.7% w/v). All films impregnated with organic acids demonstrated antimicrobial activities. Specifically, malic acid was more effective in inhibiting all three pathogens (*Listeria monocytogens*, *Salmonella*, and *E. coli* 0157:H7). In particular, the log reduction values of these pathogens were 2.48, 7.52, and 2.28 respectively. A log reduction of about 2 is very effective.

8.5 Example V

Tomato Coating

Thickness of one to six SP, WP, WG and CMC coatings of tomato ranged from 10–170, 10–33, 20–168 and 8–40 µm, respectively (Table 6). Tomato color coordinates Color L* (Lightness) a* (redness) b* (yellowness), chroma and hue angle after 1–6 coatings of WP/SP/WG/CMC coating were recorded. Redness of (a*) with 1–6 coatings of SP, WP, WG and CMC coating and without coating (control) are shown in Table 7. Redness of (a*) with 1–6 coatings of carboxymethyl cellulose, soy, whey and wheat protein coating and without coating (control) during storage up to 10 days are shown in FIGS. 4–7.

CMC coatings up to 6 times did not affect the natural color of tomato. Further, the red color of CMC coated tomatoes and non-coated tomato stored up to 10 days did not display any differences. A very thin coating (8 µm) of carboxymethyl cellulose did not mask the color of tomatoes.

Soy protein film decreased the lightness of tomatoes coated 1 to 6 times by $p<0.05$. However, the effect on lightness of tomato is not significant during storage of tomato. Soy protein film coatings also increased the redness of tomato after one coating compared to control tomatoes without coating. Specifically, soy protein film coated tomatoes were redder and yellower, higher chroma and hue angle and lower lightness after only one coating (10 µm). Soy protein film coated tomato maintained its red color during storage whereas the redness of the control tomato without coating increased with the increase in days of storage.

Whey protein coating increased lightness and decreased yellowness of tomatoes after 1 coating (10 µm) compared with control ($p<0.05$). No differences in red color of whey protein film coated and non-coated tomato were observed up to 10 days.

Wheat gluten film coating decreased redness after 2 coatings (30 µm). After 1 coating (20 µm) of whey gluten, the yellowness decreased (chroma) and lightness increased in the tomatoes. During the storage period, the redness of wheat gluten coated tomatoes was lower than control tomatoes. WG coating increased lightness of tomato Coated tomatoes maintained their color and freshness during the storage period of 10 days better than non-coated tomato. These coatings can extend the shelf-life of tomatoes, retaining the original red color during the period evaluated.

TABLE 6

Effect of number of coatings on thickness of edible film tomato surface.

| Number of coatings* | Thickness of coating (µm) | | | |
|---|---|---|---|---|
| | Soy protein | Whey Protein | Wheat protein | Carboxy methyl cellulose |
| 1 | 10** | 10 | 20 | 8 |
| 2 | 23 | 15 | 30 | 11 |
| 3 | 61 | 18 | 61 | 12 |
| 4 | 86 | 20 | 94 | 22 |
| 5 | 114 | 20 | 122 | 31 |
| 6 | 170 | 33 | 168 | 40 |

*coated to different tomatoes
**values are means of three replicates

TABLE 7

Effect of number of coatings on redness of tomato.
Color a value of (Redness) of tomato

| Coating Solution | Number of Coating | Time after first coating (h) | | | | | |
|---|---|---|---|---|---|---|---|
| | | 2 | 4 | 6 | 8 | 10 | 12 |
| Control | 0 | 19.98 | 19.79 | 19.84 | 20 | 20.51 | 20.46 |
| CMC | 1 | 19.62 | 19.38 | 19.75 | 19.44 | 19.65 | 20.09 |
| | 2 | — | 19.83 | 19.61 | 19.43 | 19.53 | 19.52 |
| | 3 | — | — | 19.93 | 19.71 | 19.7 | 19.64 |
| | 4 | — | — | — | 19.87 | 20.22 | 19.98 |
| | 5 | — | — | — | — | 19.75 | 19.64 |
| | 6 | — | — | — | — | — | 19.63 |

TABLE 7-continued

Effect of number of coatings on redness of tomato.
Color a value of (Redness) of tomato

| Coating Solution | Number of Coating | Time after first coating (h) | | | | | |
|---|---|---|---|---|---|---|---|
| | | 2 | 4 | 6 | 8 | 10 | 12 |
| Soy | 1 | 22.74* | 22.56* | 22.26* | 21.90* | 22.13*8 | 22.32* |
| | 2 | — | 22.88* | 23.38* | 23.00* | 23.30* | 23.48* |
| | 3 | — | — | 23.03* | 23.06* | 22.83* | 22.79* |
| | 4 | — | — | — | 23.62* | 23.57* | 23.41* |
| | 5 | — | — | — | — | 23.89* | 23.73* |
| | 6 | — | — | — | — | — | 23.55* |
| Wheat gluten | 1 | 18.69* | 18.79 | 18.73* | 18.85* | 19.23 | 19.34 |
| | 2 | — | 17.65* | 18.07* | 18.24* | 18.85* | 19.13 |
| | 3 | — | — | 17.22 | 17.78* | 18.07* | 18.17* |
| | 4 | — | — | — | 17.03* | 17.5* | 18.40* |
| | 5 | — | — | — | — | 16.33* | 15.16* |
| | 6 | — | — | — | — | — | 15.72* |
| Whey | 1 | 19.38 | 19.4 | 18.47* | 19.03 | 18.96* | 18.71 |
| | 2 | — | 19.53 | 19.5 | 19.26 | 19.63 | 19.32 |
| | 3 | — | — | 19.3 | 18.71 | 19.23 | 18.94 |
| | 4 | — | — | — | 19.15 | 19.34 | 18.66 |
| | 5 | — | — | — | — | 19.14 | 19.43 |
| | 6 | — | — | — | — | — | 19.38 |

All references cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

REFERENCES

1. Altekruse, S. F., Hegman, F. H., Klontz, K. C., Tombo, B. T., Tolleson, L. K. 1994. Food-borne infections in individuals wit 87:169–173.
2. Misubu, B., Hyas, A. A., Doski, C. L., Vriesencorp, F. F., Cook, S. D., Methen, F. A. 1993. Serological evidence of previous Campylobacter jejuni infection in patients with the Guillain-Barre syndrome. Ann. Intern. Med. 118: 947–953.
3. Torres, J. A. 1994. Edible films and coatings from proteins. In Hettiarachchy, N. S., Ziegler, G. R. Eds. Protein functionality in food systems, New York, Marcel Dekker Inc. pp. 467–507.
4. Ariyapitipuri, T, Mustapha, A., Clarke, A. D. 1999. Microbial shelf life determination of vacuum-packaged fresh beef treated with polylactic acid, lactic acid, and nisin solutions. J. Food Prot. 62(8):913–920.
5. Ayres, H. M. Furr, J. F., Russel, A. D. 199. Effect of permeabilizers on antibiotic sensitivity of Psuedomonas aerunosa. Leters in applied Microb. 28:13–16.
6. Boussouel, N., Mathleu, F., Benoit, V., Linder M., Revol-Junelles, M., Milliere, J. B. 1999. Response Surface Methodology, an approach to predict the effects of a lactoperoxidase system, Nisin, alone or in combination, on Listeria monocytogens in skim milk. J. Appl. Microviol. 86:642–652.
7. Brackett, R. E. 1999. Incidence, contributing factors, an control of bacterial pathogens in produce. Post Harvest Biol. Tech. 15:305–311.
8. Brody, A. L. 2002 IFT Annual Meeting & IFT Food Expo Preview, Packaging, Food Rech 56(5):112–115.
9. Brody, A. L. 2001. Produce and Technology, Packaging, Food Tech. 55:104–105.
10. Cagri, A., Ustunol, Z., Ryser E. T. 2001. Antimicrobial, mechanical and moisture barrier properties of low pH whey protein based edible films containing p-Aminobenzoic or sorbic acids. J. Food Sci. 66(6):865–870.
11. Cherington, C. A., Hinton, M., Person, G. R., Chopra, J. 1991. Short-chain organic acids at pH 5.0 kill Escherichia coli and Salmonella spp. without causing membrane perturbation. J. Appl. Bacteriol. 70:161–165.
12. Cherry, J. P. 1999. Improving the safety of fresh produce with antimicrobials. Food Tech. 53(11):54–58.
13. Chien 1999. Food preservatives organic acids and esters. Food Industries 24(8): 16–22.
14. Cutter, C. N., Siragusa, G. R. 1995a. Treatments with nisin and chelators to reduce Salmonella and E. coli on beef. J. Food Protection 57(9):1028–1030.
15. Cutter, C. N., Siragusa, G. R. 1995b. Population reduction of gram-negative pathogens following treatments with nisin and chelators under various conditions. J. Food Protection 58:977–983.
16. Fang, T. J., Heush, Y. 2000. Effect of chelators, organic acid and storage temperature on growth of E. coli 0157: H7 in ground beef treated with nisin, using response surface methodology. J. Food and Drug Analysis 8(3): 187–194.
17. Farid, M., Bala, A., Marshall, D. L. 1998. Organic acid dipping of catfish fillets: Effects o color, microbial load and Listeria monocytogens. J. Food Pros. 61(11)1470–1474.
18. Farber, J. M. and Peteerkin, P. L. 1991. Listeria monocytogens, a food-borne pathogen. Microbial Reviews 55:476–511.

19. Good, H. 2002 Solving color measurements challenges of the food industry. HunterLab. http://www.hunterlab.cimWhatsNew/Food%20Industrv.pdf accessed Jun. 28, 2003.
20. Han, J. H, 2000. Antimicrobial food packaging. J. Food tEch. 54(23)56–65.
21. Ingram M. F., Ottoway, J. H. 1956. The preservation action of acid substances. Food Chem. Ind. 42:1154–1160.
22. Lerthangkul, S. and Kroctha, J. M. 1996 Edible coating effects on post harvest quality of green bell peppers. J. of Food Sci. 61(1):176–179.
23. Miller, A. J., Call, J. E., Bowles, B. L. 1996. Sporostatic, sporocidal and heat sensitizing action of malic acid against spores of proteolytic *Clostridium botulinum*. J. Food Prot. 59(2): 115–120.
24. Padgett, T., Han, I. Y., Dawson, P. L. 1998. Incorporation of food=antimicrobial compounds into biodegradable packaging films. J. Food Prot. 61(10):1330–1335.
25. Phillips, C. A. The effect of citric acid, lactic acid, sodium citrate and sodium lactate, alone and in combination with nisin, on the growth of *Arcobacter butzleri*. Letters in Appl. Microb. 29:424–428.
26. Rhim, J. W., Gennadios, A., Handa, A., Weller, C. L., Hanna, M. A. 2000. Solubility, tensile and color properties of modified soy protein films. J. Agriculture food Chem. 48:4937–4941.
27. Richards, R. M. F., Xing, D. K. L., King, T. P. 1995. Activity of p-aminobenzoic acid compared with other organic acids against selected bacteria. J. Appl. Bact. 78(3):209–215.
28. Roe, A. J., McLaggarn, D., Davidson, I., O'Byrne, C., Booth, I. R. 1998. Perturbation of anion balance during inhibition of growth of *E. coli* by weak acids. J. Bact. 180:767–772.
29. Sirugusa, G. R., Dickson, J. S. 1993. Inhibition of *Listeria monocytogens, Salmonella Typhimurium* and *E. coli* 0157:H7 on beef muscle tissue by lactic acid or acetic acid contained in calcium alginate gels. J. Food Safety 13(2): 147–158.
30. Zhuang, R., Beuchat, I. R., Chinnan, M. S., Shewfelt, R. L., Huang, Y. W. 1996. Inactivation of *Salmonella montevideo* on tomatoes by applying cellulose-based edible films. J. Food Prot. 59(8):808–812.

What is claimed is:

1. An organic acid incorporated edible antimicrobial film comprising:
    (a) 7.0 to 16.5 grams w/w protein;
    (b) 0.63 to 1.5 grams w/w glycerol; and
    (c) 1.82 to 4.3 grams w/w at least one organic acid naturally found in fruit or lactic acid.
2. The edible film according to claim 1, wherein said protein is selected from the group consisting of soy, whey, rice bran extract, egg albumin and wheat protein.
3. The edible film according to claim 1, wherein said protein is soy protein.
4. The edible film according to claim 3, wherein said protein is present in a concentration of 10% by weight.
5. The edible film according to claim 1, wherein said glycerol is present in a concentration of 0.9% by weight.
6. The edible film according to claim 1, wherein said organic acid is selected from the group consisting of citric acid, malic acid and tartaric acid.
7. The edible film according to claim 1, wherein said organic acid is malic acid.
8. The edible film according to claim 7, wherein said malic acid is present in a concentration of 2.6% by weight.

9. An organic acid incorporated edible antimicrobial film comprising:
    (a) 1.5 to 7.5 grams w/w hydrocolloid;
    (b) 0.14 to 0.68 grams w/w glycerol; and
    (c) 0.40 to 1.95 grams w/w at least one organic acid naturally found in fruit or lactic acid.
10. The edible film according to claim 9, wherein said hydrocolloid is selected from the group consisting of carboxymethyl cellulose, alginate, carrageenan and pectin.
11. The edible film according to claim 9, wherein said hydrocolloid is carboxymethyl cellulose.
12. The edible film according to claim 10, wherein said carboxymethyl cellulose is present in a concentration of 1.5% by weight.
13. The edible film according to claim 9, wherein said glycerol is present in a concentration of 0.9% by weight.
14. The edible film according to claim 9, wherein said organic acid is selected from the group consisting of citric acid, malic acid and tartaric acid.
15. The edible film according to claim 9, wherein said organic acid is malic acid.
16. The edible film according to claim 15, wherein said malic acid is present in a concentration of 2.6% by weight.
17. The edible film according to claim 1 or 9, wherein said film is capable of inhibiting pathogens selected from the group consisting of *Listeria monocytogens, Salmonella gaminara* and *E. coli* 0157:H7.
18. A method for making an organic acid incorporated edible antimicrobial film solution comprising the steps of:
    (a) mixing protein in water wherein said protein is present in a weight ratio ranging from 7.0 to 16.5;
    (b) adding glycerol to said mixture wherein said glycerol is present in a weight ratio ranging from 0.63 to 1.5;
    (c) heating said mixture to 60° to 85° C. for 30 minutes thereby creating a solution; and
    (d) adding at least one organic acid naturally found in fruit or lactic acid to said solution wherein said organic acid is present in a weight ratio ranging from 1.82 to 4.3.
19. The method according claim 18, wherein said mixture is heated to 85° C. for 30 minutes.
20. The method according claim 18, further comprising lowering the pH of said solution to a pH of about 3.3.
21. The method according claim 18, further comprising lowering the pH of said solution to a pH of about 3.3 using malic acid.
22. The edible film according to claim 18, wherein said organic acid is selected from the group consisting of citric acid, malic acid and tartaric acid.
23. The method according to claim 18, wherein said organic acid is malic acid.
24. The method according to claim 23, wherein said malic acid is present in a concentration of 2.6% by weight.
25. The method according to claim 18, wherein said protein is selected from the group consisting of soy, whey, rice bran extract, egg albumin and wheat protein.
26. The method according to claim 18, wherein said protein is soy protein.
27. The method according claim 26, wherein said soy protein is present in a concentration of 10% by weight.
28. A method for making an organic acid incorporated edible antimicrobial film solution comprising the steps of:
    (a) mixing hydrocolloid in water wherein said hydrocolloid is present in a weight ratio ranging from 1.5 to 7.5;
    (b) adding glycerol to said mixture wherein said glycerol is present in a weight ratio ranging from 0.14 to 0.68;
    (c) heating said mixture to 60° to 85° C. for 30 minutes thereby creating a solution; and (d) adding at least one organic acid naturally found in fruit or lactic acid to said solution wherein said organic acid is present in a weight ratio ranging from 0.40 to 1.95.

29. The method according claim 28, wherein said mixture is heated to 85° C. for 30 minutes.

30. The method according claim 28, further comprising lowering said solution to a pH of about 3.3.

31. The method according claim 28, further comprising lowering said solution to a pH of about 3.3 using malic acid.

32. The method according claim 28, wherein said glycerol is present in a concentration of 0.9% by weight.

33. The method according claim 28, wherein said organic acid is selected from the group consisting of citric acid, malic acid and tartaric acid.

34. The method according claim 28, wherein said organic acid is malic acid.

35. The method according claim 34, wherein said malic acid is present in a concentration of 2.6% by weight.

36. The method according claim 28, wherein said hydrocolloid is selected from the group consisting of carboxymethyl cellulose, alginate, carrageenan and pectin.

37. The method according claim 28, wherein said hydrocolloid is carboxyl methylcellulose.

38. The method according claim 37, wherein said carboxymethyl cellulose is present in a concentration of 1.5% by weight.

39. A method for coating comestible products with an organic acid incorporated edible antimicrobial film solution comprising the steps of:
(a) mixing hydrocolloid in water wherein said protein is present in a weight ratio ranging from 1.5 to 7.5;
(b) adding glycerol to said mixture wherein said glycerol is present in a weight ratio ranging from 0.14 to 0.68
(c) heating said mixture to 60° to 85° C. for 30 minutes thereby creating a solution;
(d) adding at least one organic acid naturally found in fruit or lactic acid to said solution wherein said organic acid is present in a weight ratio ranging from 0.40 to 1.95; and
(e) applying said solution to said comestible product at a thickness in the range of 8–40 μm.

40. The method according claim 39, wherein said mixture is heated to 85° C. for 30 minutes.

41. The method according claim 39, further comprising lowering said solution to a pH of about 3.3.

42. The method according claim 39, further comprising lowering said solution to a pH of about 3.3 using malic acid.

43. The method according claim 39, wherein said glycerol is present in a concentration of 0.9% by weight.

44. The method according claim 39, wherein said organic acid is selected from the group consisting of citric acid, malic acid and tartaric acid.

45. The method according claim 39, wherein said organic acid is malic acid.

46. The method according claim 45, wherein said malic acid is present in a concentration of 2.6% by weight.

47. The method according claim 39, wherein said hydrocolloid is selected from a group consisting of carboxymethyl cellulose, alginate, carrageenan and pectin.

48. The method according claim 39, wherein said hydrocolloid is carboxyl methylcellulose.

49. The method according claim 48, wherein said carboxymethyl cellulose is present in a concentration of 1.5% by weight.

50. A method for coating comestible products with an organic acid incorporated edible antimicrobial film solution comprising the steps of:
(a) mixing protein in water wherein said protein is present in a weight ratio ranging from 7.0 to 16.5;
(b) adding glycerol to said mixture wherein said glycerol is present in a weight ratio ranging from 0.63 to 1.5
(c) heating said mixture to 60° to 85° C. for 30 minutes thereby creating a solution;
(d) adding at least one organic acid naturally found in fruit or lactic acid to said solution wherein said organic acid is present in a weight ratio ranging from 1.82 to 4.3; and
(e) applying said solution to said comestible product at a thickness in the range of 10–168 μm.

51. The method according claim 50, wherein said mixture is heated to 85° C. for 30 minutes.

52. The method according claim 50, further comprising lowering said solution to a pH of about 3.3.

53. The method according claim 50, further comprising lowering said solution to a pH of about 3.3 using malic acid.

54. The method according claim 50, wherein said organic acid is selected from the group consisting of citric acid, malic acid and tartaric acid.

55. The method according claim 50, wherein said organic acid is malic acid.

56. The method according claim 55, wherein said malic acid is present in a concentration of 2.6% by weight.

57. The method according claim 50, wherein said protein is selected from the group consisting of soy, whey, rice bran extract, egg albumin and wheat protein.

58. The method according claim 50, wherein said protein is soy protein.

59. The method according claim 58, wherein said protein is present in a concentration of 10% by weight.

* * * * *